United States Patent [19]

Fuller et al.

[11] Patent Number: 4,842,999

[45] Date of Patent: Jun. 27, 1989

[54] CANINE HEARTWORM VACCINE AND DIAGNOSTIC TEST

[75] Inventors: Steven A. Fuller; John G. R. Hurrell, both of Georgetown, Canada

[73] Assignee: ADI Diagnostics Inc., Rexdale, Canada

[21] Appl. No.: 895,450

[22] Filed: Aug. 11, 1986

[51] Int. Cl.$^4$ .......................................... G01N 33/577
[52] U.S. Cl. .......................................... 435/7; 424/88; 530/395; 530/387; 530/820; 436/548; 435/68; 435/240.27; 435/948
[58] Field of Search ................ 435/7, 68, 240.27, 948; 424/88; 530/395, 300; 436/518

[56] References Cited

U.S. PATENT DOCUMENTS

| | | | |
|---|---|---|---|
| 4,322,495 | 3/1982 | Kato | 435/7 |
| 4,430,329 | 2/1984 | Blair | 424/181 |
| 4,568,639 | 2/1986 | Lew | 435/68 |
| 4,656,251 | 4/1987 | Mosier | 424/88 |

FOREIGN PATENT DOCUMENTS 3609584  11/1984  Australia .

OTHER PUBLICATIONS

Boto et al., "Antigens to Dirofilaria Immitis Which Are Immunogenic in the Canine Host: Detection by Immuno-Staining of Protein Blots with the Antibodies of Occult Dogs." J. Immunol: 133 (1984) 975-980.

Boto et al., "Homologous and Distinctive Antigens of Onchocerca Volvulus and Dirofilaria Immitis: Detection by an Enzyme-Linked Immuno-Inhibition Assay" J. Immunol: 133 (1984) 981-987.

Gillis et al., Am J Vet Res, 45:2289-2292 (1984).

Hamilton et al., Experimental Parasitology, 56:298-313 (1983).

Matsumura et al., Immunology, 51:609-613 (1984).

Rawlings et al., JAVMA, 180:1323-1326 (1982).

Scholtens et al., Am. J. Vet Res, 44:861-864 (1983).

Weil, et al., Am J. Trop. Med. Hyg., 33:425-430 (1984).

Weil et al., Journal of Immunology, 134:1185-1191 (1985).

Wong et al., Experimental Parasitology, 35:465-474 (1974).

Knott, J., Transactions of the Royal Society of Tropical Medicine and Hygiene, 33:191-196 (1939).

Primary Examiner—Christine M. Nucker
Attorney, Agent, or Firm—Saidman, Sterne, Kessler & Goldstein

[57] ABSTRACT

This invention relates to a vaccine for canine heartworm. The invention further relates to a diagnostic test capable of discerning the presence of the canine heartworm parasite even in occult infections. The invention discloses kits and test strips suitable for diagnosing canine heartworm infections.

5 Claims, No Drawings

CANINE HEARTWORM VACCINE AND DIAGNOSTIC TEST

FIELD OF THE INVENTION

This invention relates to a vaccine for canine heartworm. The invention further relates to a diagnostic test capable of discerning the presence of the canine heartworm parasite.

BACKGROUND ART

Canine heartworm disease is caused by the parasite, *Dirofilaria immitis* (*D. immitis*). This parasite is transmitted to dogs via a mosquito vector. Infective *D. immitis* larvae, which have developed in infected mosquitos, enter the dog through the mosquito bite wound. Upon entering the dog's circulatory system, the larvae develop and migrate to the dog's heart where they mature and breed. *Dirofilaria immitis* young, termed "microfilariae," migrate throughout the dog's circulatory system, where they may be ingested by a mosquito that feeds upon the infected dog. The *Dirofilaria immitis* life cycle is completed when the ingested microfilariae mature into infective larvae in the mosquito.

The physical presence of the heartworm parasite in the pulmonary artery and right ventricle of the canine heart, and the resulting destruction of tissue, causes respiratory and circulatory problems which can be fatal under conditions of stress or vigorous exercise. The heartworm parasite has also been shown to be the cause of focal lung, liver, eye and cutaneous lesions in man (Hamilton, R.G., et al., *Exper. Parasitol.*, 56:298–313 (1983)).

Diagnosis of canine heartworm has, traditionally, been accomplished by the identification of *D. immitis* microfilariae in blood samples of dogs (Knott, J., *Trans. Roy. Soc. Trop. Med. Hyg.*, 33: 191–196 (1939); Weiner, D. J. et al., *Bull. S. E. Assoc. Biol.*, 17:69 (1970)). A major obstacle to accurate diagnosis is the fact that approximately 35% of heartworm-infected dogs suffer from what is known as an "occult" infection, in which no circulating microfilariae are observed. Occult infections may occur if either: (1) the heartworm infection has not progressed to the stage at which microfilariae are detectable; (2) an animal has been infected with *D. immitis* of only a single sex; (3) the infective *D. immitis* parasites are sterile; or (4) if the infection is an immune-mediated sterile infection (Rawlings, C. A. et al., *J. Amer. Veter. Med. Assoc.*, 180:1323–1326 (1982)).

The significance of canine heartworm infection, and the importance of its accurate diagnosis even in occult cases, have led to the development of alternative methods for diagnosing canine heartworm infection. Kato, K. H. (U.S. Patent No. 4,322,495) discloses an immunoassay capable of detecting antibodies which are produced by the dog in response to the canine heartworm infection. The antibodies detected by the method of Kato comprise an unfractionated collection of immunoglobulins directed against the surface antigens of the heartworm parasite. Because this immunoassay tests for the presence of anti-heartworm antibodies, the test is useful in diagnosing both occult and overt stages of canine heartworm disease.

The diagnostic potential of this approach may be limited by the low titers of anti-heartworm antibodies which are observed in many occult heartworm infections (Scholtens, R. G., et al., *Amer. J. Vet. Res.*, 44:861–864 (1983)). Moreover, interference from low affinity, cross-reacting canine antibodies has been found to increase the percentage of false-positive results (Gillis, J. M., et al., *Amer. J. Vet. Res.*, 45:2289–2292 (1984)).

The deficiencies of the above described methods spurred further research aimed at developing an alternative procedure for diagnosing canine heartworm disease Weil, G. J., et al., (Amer. J. Trop. Med. Hyg., 33:425–430 (1984)) discovered that *D. immitis* infections could be diagnosed by the presence of parasitespecific antigens in circulating blood. Thus, according to the method of Weil, et al., an immunological reaction between a standardized antisera (containing antibodies against the *D. immitis*'s antigens) and the sera of potentially infected dogs would indicate that a canine heartworm infection was present. Subsequent work revealed that two *D. immitis*' antigens (having molecular weights greater than 100,000 daltons) were the sole immunogenic proteins identified in the Weil, et al., immunoassay (Weil, G. J., *Immunol.*, 134:1185–1191 (1985)). Hybridoma cell lines that produce monoclonal antibodies specific for these antigens were obtained and characterized by Weil, and his co-workers (Weil, G. J., et al., (1985), supra). Patent applications describing this work have been filed in the United States (Ser. No. 557,117) and Australia (Application No. 8,436,095). The immunoassay developed by Weil is currently commercialized as the FILAROCHEK TM CANINE HEARTWORM ANTIGEN TEST KIT of MALLINCKRODT, Inc., N.Y.

If accurately diagnosed in its early stages, heartworm disease can be successfully treated. Currently, heartworm disease is treated by administering anti-parasitic agents to infected animals (Blair, L. S., U.S. Pat. No. 4,430,329). Unfortunately, heartworm disease which has not been diagnosed in its early stages may be quite refractile to treatment. For this reason, researchers have attempted to identify compositions which could serve as a preventive vaccine. As discussed above, the life cycle of *D. immitis* requires both canine and mosquitoe hosts. The third larval stage (L3) of the heartworm parasite, found predominantly in mosquitoes, has been found to produce antigens which are capable of inducing an immunogenic response in dogs. (Wong, M. M., et al., *Exper. Parasitol.*, 35:465–474 (1974)).

Wong, M. M. and co-workers irradiated L3 *D. immitis* larvae with X-rays, and introduced the irradiated larvae into dogs. The "vaccinated" dogs were found to produce low titers of anti-heartworm antibodies. When challenged with infective, non-irradiated L3 larvae, only 50% of the "vaccinated" animals exhibited any clinical signs of heartworm infection. The high cost of maintaining populations of live worms in experimental dogs and large colonies of vector mosquitoes, has, thus far, precluded commercial applications of the Wong "vaccine" (Wong, M. M., et al., supra).

The difficulty of producing heartworm antigens in an easily cultured microorganism was addressed by Lew K. K. (U.S. Pat. No. 4,568,639). Lew discloses the possibility of modifying an easily cultured helminth so as to enable it to produce the desired *D. immitis* antigens. Once such a genetically modified helminth was obtained, Lew discloses that the genes which encode the antigen could be cloned, and the antigen purified. Using his method, Lew succeeded in isolating a mutant derivative of the nematode *Caenorhabditis elegans* which could be used in the diagnosis of canine heartworm infections.

Thus, in summary, the prior art discloses the significance of diagnostic tests and preventive vaccines for canine heartworm disease. Diagnostic tests which are based upon the identification of either heartworm antigen, or canine antibodies directed against heartworm antigens, have been developed. The difficulty of culturing *D. immitis* in its canine and mosquito hosts has made the development of a commercializable and efficacious vaccine a difficult and, thus far, elusive task.

SUMMARY OF INVENTION

The present invention is based upon the discovery of an immunologically active protein which is useable as a vaccine against canine heartworm disease. The invention additionally provides a method for diagnosing canine heartworm disease, even when present as an occult infection. In greater detail, the invention comprises:

A polypeptide associated with *D. immitis* having a molecular weight selected from the group consisting of: approximately 14 kd, approximately 58 kd, approximately 66 kd and approximately 90 kd, wherein the protein is substantially free of natural contaminants.

The invention additionally relates to a vaccine usable for the prevention of canine heartworm disease, comprising an immunologically active polypeptide associated with *D. immitis*, the polypeptide being substantially free of natural contaminants and having a molecular weight selected from the group consisting of: approximately 14 kd, approximately 58 kd, approximately 66 kd and approximately 90 kd, together with a carrier.

The invention also pertains to a method for preventing canine heartworm disease which comprises providing to a susceptible animal an effective amount of a composition which comprises (A) an immunologically active polypeptide associated with *D. immitis*, the polypeptide being substantially free of natural contaminants and having a molecular weight selected from the group consisting of: approximately 14 kd, approximately 58 kd, approximately 60 kd and approximately 90 kd, together with (B) a carrier.

The invention is also directed to an antibody capable of binding to an immunologically active polypeptide associated with *D. immitis*, the polypeptide having a molecular weight selected from the group consisting of: approximately 14 kd, approximately 58 kd approximately 66 kd and approximately 90 kd, wherein the antibody is substantially free of natural contaminants.

The invention also pertains to the cell lines: IDi10 which produces the IDi10 monoclonal antibody directed against the 14 kd *D. immitis* antigen, and IDi76 which produces the IDi76 monoclonal antibody directed against the GPA proteins. These cell lines were deposited with the American Type Culture Collection (ATCC), Rockville, Md., on August 4, 1986 and given the designations ATCC No. HB 9164 and ATCC No. 9163, respectively.

Also provided is a method for diagnosing *D. immitis* infection which comprises examining an animal for the presence of a polypeptide associated with *D. immitis* having a molecular weight selected from the group consisting of approximately 14 kd, approximately 58 kd, approximately 66 kd, and approximately 90 kd.

The invention further provides a method for diagnosing *D. immitis* infection which comprises examining an animal for the presence of an anti-*D. immitis* antibody, the antibody being capable of binding to a polypeptide associated with *D. immitis*, the polypeptide having a molecular weight selected from the group consisting of approximately 14 kd, approximately 58 kd, approximately 66 kd, and approximately 90 kd.

The invention also provides a method for diagnosing *D. immitis* infection by immunoassay which comprises:

(A) providing to a sample suspected of containing an anti-*D. immitis* antibody, a polypeptide as described above capable of being bound by the antibody, the polypeptide being bound to a solid support;

(B) providing to the sample a second antibody, the second antibody being detectably labeled and being capable of binding the anti-*D. immitis* antibody; and (C) determining the amount of the anti-*D. immitis* antibody present in the sample by measuring the amount of the second antibody bound to the solid support.

The invention also provides a test strip useful for carrying out the above methods which comprises a solid support means, said support means being coupled to a polypeptide associated with *D. immitis* having a molecular weight selected from the group consisting of: approximately 14 kd, approximately 58 kd, approximately 66 kd and approximately 90 kd.

DESCRIPTION OF THE PREFERRED EMBODIMENTS

The present invention is based upon the discovery that canine heartworm infections may be diagnosed by assaying for the presence of certain antigenic *D. immitis* polypeptides.

Certain terms which are utilized in the specification and claims are defined as follows in order to provide consistent understanding thereof.

A material is said to be "substantially free of natural contaminants" if it has been substantially purified from materials with which it is normally and naturally found. Examples of natural contaminants with which canine heartworm antigens might be associated are: other peptides, free carbohydrates, other glycosylated peptides, lipids, membrane, etc. A material is also said to be substantially free of natural contaminants if these contaminants are substantially absent from a sample of the material.

The term "peptide fragment" is meant to include both synthetic and naturally-occurring amino acid sequences derivable from a naturally occurring amino acid sequence.

A polypeptide is said to be "associated" with a particular organism if it can be naturally found in association with the particular organism or is derivable from the particular organism.

A polypeptide is said to be "derivable from a naturally-occurring amino acid sequence" if it can be obtained by fragmenting a naturally-occurring chosen sequence, or if it can be synthesized based upon a knowledge of the chosen sequence or of the genetic material (DNA or RNA) which encodes this sequence.

As used herein, a protein or polypeptide is said to be "immunologically active" if it is capable of causing the initiation of an immunogenic response in an animal. Such a response may include the induction of antibody synthesis directed against the immunologically active protein.

An immunologically active protein or polypeptide is said to be "usable as a vaccine" if its introduction into an animal results in the production of an antibody which is active against (i.e. capable of reacting with, or neutralizing) a disease-causing agent. Hence, the administration of such a protein or polypeptide to a susceptible animal is capable of providing an otherwise susceptible animal with protection from the disease causing agent. An animal is said to be susceptible to a disease-causing agent if that animal belongs to a species capable of contracting a disease associated with the presence of the disease-causing agent.

A *D. immitis* antigen is said to be "secreted or excreted" if that antigen is normally and naturally found in free form (i.e. unattached to a *D. immitis* microorganism) in the external environment (i.e. culture media, serum, etc.) in which the parasite is growing.

The *D. immitis* antigens of the present invention are divisible into two classes. The first class termed "excretory-secretory protein ("ESP")" is naturally shed by adult worms. Thus ESP may be obtained by maintaining adult worms in cell culture media. Any media suitable for maintaining *D. immitis* worms may be used. However, it is preferable to use a growth media consisting of Dulbecco's Modified Eagle's Medium with 4.5 g/l glucose, 20 mM L-glutamine. The medium contains no serum. The media is changed daily and the ESP is collected by ultra filtration using an Amicon ™ YM5 membrane. ESP then, is a limited subset of all total proteins that would be found in a crude worm extract. It has major protein components of 14, 16, 18 and 20–22 kd. Glycoprotein antigens are also a component of ESP, but are much less prominent than those mentioned. The 14 kd ESP is produced by L3 larvae, and *D. immitis* microfilariae and adults.

The second class of antigens which is provided by the present invention consists of "glycoprotein antigens" ("GPA"). A "glycoprotein" is a polypeptide which contains covalently bonded sugar residues. These antigens are obtainable from crude extracts of whole adult *D. immitis* worms. Crude extracts of adult *D. immitis* worms were prepared by homogenizing the worms in two volumes of phosphate buffered saline (10mM sodium phosphate, 0.15M sodium chloride pH 7.2) using a tissue grinder. Debris was removed by centrifugation and the supernatant collected and termed "adult worm crude extract".

The antigenic polypeptides which may be used according to the present invention are any of a complex series of antigens having molecular weights of either 14, 58, 66 or 90 kd or fragments thereof. It is especially preferable to assay for *D. immitis* antigens which are expressed in all stages of the canine-borne *D. immitis* parasite. It is further preferable to diagnose canine heartworm disease by assaying for the presence of a secreted or excreted *D. immitis* antigen. The invention may be performed by assaying for the presence of 14, 58, 66, or 90 kd *D. immitis* antigens. It is, however, most preferable to diagnose canine heartworm infections by assaying for the presence of the 58, 66 or 90 kd GPA *D. immitis* antigen.

Included within the scope of the present invention are those amino acid sequences in the above polypeptides which are capable of functioning as heartworm vaccines or diagnostic aids. Included as well are the use of additional amino acid residues added to enhance coupling to carrier protein or amino acid residues added to enhance the therapeutic or diagnostic effect.

The present invention is intended to include any peptide derivable from the amino acid sequence of any *D. immitis* antigen disclosed herein.

The invention further pertains to polypeptides that, in addition to the chosen sequence, may contain or lack one or more amino acids that may not be present in the naturally-occurring sequence or which may lack some or all of the carbohydrate normally associated with the anti-peptide, or which contain patterns of glycosylation which differ from those normally associated with the polypeptide as long as the polypeptides are functionally similar to the chosen polypeptide. Such polypeptides for the present invention are termed "functional derivatives," provided that they demonstrate activity which is substantially similar to that of the above-described heartworm antigen.

As is known in the art, the amino acid residues may be in their protected or unprotected form, using appropriate amino or carboxyl protecting groups.

Variable length peptides may be in the form of the free amines (on the N-terminus), or acid-addition salts thereof. Common acid addition salts are hydrohalic acid salts, i.e., HBr, HI, or more preferably, HCl.

In one embodiment of the present invention, canine heartworm disease may be diagnosed by assaying the ability of antibodies (capable of specifically binding to the *D. immitis* antigen) to undergo an immunological reaction with fluid samples (such as blood, lymph, etc.) of a susceptible host animal. This embodiment is an assay for *D. immitis* antigens.

A second embodiment of the invention provides a method for diagnosing canine heartworm disease by assaying for the presence of antibodies which are directed against any of the above described *D. immitis* antigens. As would be apparent to one of ordinary skill in the art, a wide variety of different immunological assays and techniques may be adapted to accomplish these goals of the present invention.

I. Immunoassays for the *D. Immitis* Antigen and for Antibody Therefor

In assaying for antigen, one uses binding assays which utilize binding molecules, such as antibodies.

Binding molecules of the present invention may be utilized for any of the immunoassays wherein antibodies have been previously used. In one embodiment, the binding molecules are detectably labeled, utilizing conventional labeling techniques well known to the art. Thus, the binding molecules may be radiolabeled using, for example, radioactive isotopes such as $^3$H, $^{125}$I, $^{131}$I and $^{35}$S.

The binding molecules may also be labeled using fluorescent labels, enzyme labels, free radical labels, or bacteriophage labels, using techniques known in the art.

Typical fluorescent labels include fluorescein isothiocyanate, rhodamine, phycoerythrin, phycocyanin, alophycocyanin, and Texas Red.

Suitable enzymes include alkaline phosphatase, urease, beta-galactosidase, glucose-6-phosphate dehydrogenase, maleate dehydrogenase, and peroxidase.

Two principal types of enzyme immunoassays are the enzyme-linked immunosorbent assay (ELISA), and the homogeneous enzyme immunoassay, also known as enzymemultipled immunoassay (EMIT). In the ELISA system, separations may be achieved, e.g., by the use of antibodies coupled to a solid phase. The EMIT system depends on deactivation of the enzyme in the traceranti-body complex; the activity can thus be measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labeling, the bioluminescent compounds including luciferin, luciferase, and aequorin.

Once labeled, the binding molecule may be employed to detect, i.e. to identify and/or quantify immunologic counterparts utilizing techniques well-known to the art. Thus in the present invention the term "detect" includes identification of the presence of the molecule or functional group and also includes quantifying same.

A good description of a radioimmune assay (RIA) may be found in *Laboratory Techniques and Biochemistry in Molecular Biology*, by Work, T. S., et al., with particular reference to the chapter entitled "An Introduction to Radioimmune Assay and Related Techniques" by Chard, T., North Holland Publishing Company, New York, N.Y. (1978), incorporated by reference herein.

The binding molecules of the present invention may also be adapted for utilization in an immunometric assay, also known as "2-site" or "sandwich" assays. In a typical immunometric assay, a quantity of unlabeled antibody is bound to a solid support that is insoluble in the fluid being tested and a quantity of soluble antibody bearing a label that permits detection and/or quantitation of the ternary complex formed between solid phase antibody, antigen, and labeled antibody is added.

Typical immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody. After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. These "2-site" or "sandwich" assays are described by Wide at pages 199–206 of "Radioimmune Assay Method," edited by Kirkham and Hunter, E. & S. Livingstone, Edinburgh, 1970.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplex labeled antibody. The presence of labeled antibody associated with the solid support is then determined as it would be in a conventional "forward" sandwich assay.

In the reverse assay, step wise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the simultaneous and forward assays.

As explained above, the immunometric assays for antigen require that the particular binding molecule be labeled with a "reporter molecule." These reporter molecules or labels, as identified above, are conventional and well known to the art. In the practice of the present invention, enzyme labels are a preferred embodiment. No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as labels in the immunometric assays of the present invention are horseradish peroxidase, alkaline phosphatase, beta-D-galactosidase, urease, glucose oxidase, glucoamylase, carbonic anhydrase, acetylcholinesterase, lysozyme, malate dehydrogenase, and glucose-6-phosphate dehydrogenase. Urease is among the preferred enzyme labels, particularly because of chromogenic pH indicators which make its activity readily visible to the naked eye.

The labeled binding molecule or antibody of the present invention may be prepared using techniques well known in the art. Typical techniques are described by Kennedy, J. H., et al., *Clin. Chim. Acta*, 70:1–31 (1976) and Schuurs, A.H.W.M., et al., *Clin. Chim. Acta*, 81:1–40 (1977). Coupling techniques mentioned in the latter are the glutaraldehyde method, the periodate method, the dimaleimide method, the m-maleimidobenzyl-N- hydroxy-succinimide ester method, all these methods are incorporated by reference herein.

The monoclonal antibodies of the present invention may be produced by adapting the method of Kohler, et al., (*Nature*, 256:495–497 (1975)). Thus, to obtain the monoclonal antibodies of the present invention, one immunizes mice, preferably BALB-c mice with an amount of *D. immitis* antigen capable of eliciting an immunogenic response. Although other means may be employed, it is preferable to immunize mice by an intraperitoneal injection of between 5–200 ug of *D. immitis* antigen. If necessary, the immunogenic response of the mice may be increased through the intravenous or intraperitoneal injection of a booster dose of *D. immitis* antigen administered two to three months after the initial immunization. The booster dose is preferably between 5–50 ug. Approximately two to three months after the initial immunization, the mice are sacrificed and a spleen cell suspension is prepared in the manner taught by Gerhard, et al., (Eur J. Immunol., 5:720–725 (1975)). Hybridoma cells, capable of producing the monoclonal antibodies of the present invention, are formed by fusing the above described spleen cells with a myeloma cell line such as the MOPC-21 line described by Kohler, et al., (supra) or, preferably, the SP2/0 myeloma cell line described by Schulman, M. et al. (*Nature*, 276:269–270 (1978)). Those hybridoma cell lines which produce monoclonal antibodies directed against *D. immitis* antigens are identified by incubating the immunoglobulins produced by the obtained hybridoma cell lines with purified *D. immitis* antigen. Hybridoma cell lines which produce anti-*D. immitis* antibodies react with these antigens, and thereby permit the identification, purification and propagation of the desired monoclonal antibody producing cell lines.

As used herein, an effective amount of a diagnostic reagent (such as an antibody or an antigen) is one capable of achieving the described diagnostic discrimination. The amount of antibody used in a diagnostic test is generally between 0.01–1 ug, and preferably between 0.1–1 ug. The amount of antigen used in a diagnostic assay is typically between 0.01–1 ug, and preferably between 0.1–1 ug.

The present invention alternatively provides a method for detecting the presence of antibodies which are specific to D. immitis antigens. The presence of such antibodies in the sera of an animal would be indicative of that animal's prior or present exposure to the canine heartworm parasite. Thus, an immunoassay based upon the detection and quantitation of anti-D. immitis antibodies provides an alternative method for diagnosing canine heartworm disease. Such an immunoassay may be performed by adapting the method of Fridlender, B. R. (U.S. Pat. No. 4,313,927). Thus, purified D. immitis antigen is coupled or bound to a solid surface. Any of the above described coupling techniques may be modified to accomplish this goal. The immobilized surface to which the antigen is bound may be chosen from a wide variety of possible surfaces such as nylon, latex, glass, silica, polyethylene, polystyrene, polyvinyl chloride or polycarbonate. The support material may have virtually any possible structural configuration so long as the coupled antigen is capable of binding to any D. immitis antibody which is provided. Thus, the support configuration may be spherical, as in a bead, or cylindrical as in the inside surface of a test tube, or the external surface of a rod. Alternatively, the surface may be flat such as a sheet, test strip, etc.

In order to assay for the presence of an anti-D. immitis antibody, bound D. immitis antigen (as described above) is incubated in a manner sufficient to permit an immunological reaction (Work, T. S., et al., supra) with a sample of sera or other fluid suspected of containing D. immitis antibodies. Thus, any antibodies specific to the bound D. immitis antigen will bind to that antigen and thereby become immobilized onto the solid surface. After allowing this incubation to continue for a period of time between 1–30 minutes the bound antigen-solid surface (to which any D. immitis antibody has been bound) is extensively washed to remove any unbound D. immitis antibodies which may be present in the sample. The presence of these unbound antibodies may reflect the fact that the sample contains an amount of D. immitis antibodies which exceeded the binding capacity of the bound D. immitis antigens. Alternatively, the presence of unbound antibodies may reflect the fact that the immunoassay has not proceeded to completion.

The washed solid support (described above) is then incubated in the presence of a second antibody which is capable of binding to the bound D. immitis specific antibody. This second antibody may therefore be an immunoglobulin specific for the particular D. immitis antibody bound to the solid surface ("an anti-anti-D. immitis antibody"). Alternatively, the second antibody may be one capable of reacting with any antibody derived from the species which provided the fluid sample. Thus, if, for example, one wished to assay for the presence of D. immitis antibodies from a sample of canine fluid, then the second antibody could be either an anti-anti-D. immitis antibody, an anti-canine antibody, or an antibody with substantial cross-reactivity with canine antibodies.

According to the present invention, the second antibody used in the above described immunoassay is incubated in the presence of the solid surface-anti- gen-bound D. immitis antibody complex under conditions sufficient to permit the second antibody to bind to the complexed first antibody. After permitting such an incubation period the solid surface is washed and the amount of the second antibody which has bound to the complexed D. immitis antibody is determined. Since the second antibody may become affixed to the solid surface only through its binding to the bound D. immitis antibody, the amount of the second antibody which has become bound to the solid surface is indicative of and proportional to the concentration of anti-D. immitis antibody which was present in the fluid sample being examined. Thus, in accord of the present invention the amount of the anti-D. immitis antibody present in a fluid sample is determined by measuring the amount of a second antibody which has become bound to it. To accomplish this measurement, it is desirable for the second antibody to be detectably labeled. A wide variety of labels may be employed in accord with the present invention. Thus, for example, the second antibody may be radiolabeled with radioisotopes such as $^{14}C$, $^{125}I$, or the like. Alternatively, chemical groups capable of undergoing fluorescence may be coupled to the second antibody, which may then be detectable by fluorescence emmissions. Suitable fluorescent labels and coupling techniques have been described above. The second antibody may, alternatively, be labeled with an enzyme, such as those described above. As would be obvious to one of ordinary skill in the art, any means for detectably labeling the second antibody which would permit one to detect or quantitate the amount of bound second antibody could be used in accord with the present invention.

II. Vaccine Compositions Utilizing the D. Immitis Antigen

In addition to providing a method for diagnosing canine heartworm infection, the present invention also provides a means for preventin the onset of such infections and for treating infected animals. One discovery of the present invention is the fact that compositions containing a D. immitis antigen (having a molecular weight of either 14, 58, 66 or 90 kd) are suitable as vaccine. Thus, the administration of such an antigen results in the synthesis of antibodies capable of binding to and neutralizing the heartworm parasite. Although, any such D. immitis antigen which is capable of eliciting the formation of anti-heartworm antibodies may be used, it is preferable to use as a vaccine candidate a 14 kd antigenic protein of the canine heartworm parasite.

The present invention also provides a means for passively treating animals infected by the canine heartworm parasite. In this embodiment of the invention, antisera capable of specifically binding to a D. immitis antigen is introduced into an infected animal (as by injection).

As would be understood by one of ordinary skill in the art, a vaccine composition may contain salts, buffers, adjuvants, or other substances which are desirable for improving the efficacy of the vaccine composition. Adjuvants are substances that can be used to specifically augment a specific immune response. Normally, the adjuvant and the antigen are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, AlK(SO$_4$)$_2$, AlMa(SO$_4$)$_2$, AlNH$_4$(SO$_4$), silica, kaolin, and carbon), polynucleotides (for example poly IC and poly AU acids), and certain natural substances (for example, wax D from *Mycobacterium tuberculosis,* as well as substances found in *Corynebacterium parvum,* or *Bordetella pertussis,* and members of the *genus Brucella.* Among those substances particularly useful as adjuvants are the saponins such as, for example, Quil A. (Superfos A/S, Denmark). Examples of materials suitable for use in vaccine compositions are provided in *Remington's Pharmaceutical Sciences* (Osol, A., Ed., Mack Publishing Co., Easton, Pa. pp 1324–1341 (1980)).

The vaccine composition can be administered parenterally by injection, rapid infusion, nasopharyngeal absorption (intranasopharangeally), dermoabsorption, or orally. The vaccine composition may alternatively be administered intramuscularly, or intravenously. Preparations for parenteral administration include sterile or acculas or non-aqueous solutions, suspensions, and emulsions. Examples of non-aqueous solvents are propylene glycol, polyethylene glycol, vegetable oils such as olive oil, and injectable organic esters such as ethyl oleate. Carriers or occulsive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containg inert diluents commonly used in the art, such as purified water. Besides the inert diluents, such compositions can also include adjuvants, wetting agents, emulsifying and suspending agents, or sweetening, flavoring, or perfuming agents.

Many different techniques exist for the timing of the immunizations when a multiple immunization regimen is utilized. It is possible to use the antigenic preparation of the invention more than once to increase the levels and diversities of expression of the immunoglobulin repertoire expressed by the immunized animal. Typically, if multiple immunizations are given, they will be given one to two months apart.

According to the present invention, an "effective amount" of a vaccine is one which is sufficient to achieve a desired biological effect. Generally, the dosage of the vaccine composition administered in an animal which comprises an effective amount of the vaccine will vary depending upon such factors as the animal's age, condition, sex, and extent of disease, if any, and other variables which can be adjusted by one ordinary skill in the art.

The antigenic preparations of the invention can be administered by either single or multiple dosages of an effective amount. Effective amounts of the compositions of the invention can vary from 0.01–1,000 ug/ml per dose, more preferably 0.1–500 ug/ml per dose, and most preferably 10–300 ug/ml per dose.

Having now generally described this invention, the same will be the better understood by reference to certain specific examples which are included herein for purposes of illustration only and are not intended to be limiting of the invention, unless specified.

EXAMPLE I

Preparation of *D. immitis* ESP

*D. immitis* worms were grown in Dulbecco's Modified Eagle's Medium (supplemented with 4.5 g/l glucose, 20 mM HEPES, and 2 mM L-glutamine), for 2–4 weeks at 37° C. in 8% CO$_2$. The media was changed daily. Samples of culture media were removed daily and excretory-secretory proteins were removed by ultrafiltration. The supernatant material was subjected to either 12% or 15% SDS-polyacrylamide gel electrophoresis and transferred to nitrocellulous paper (Millipore HAHY 000 01). Sera from heartworm-infected or non-infected dogs were incubated with these nitrocellulous papers. Antigens recognized only by antibodies present in infected dog serum were visualized through the use of an anti-canine-IgG (Allelix) followed by goat anti-mouse IgG-peroxidase (Cappel). The desired ESP antigens were eluted from the gel and purified.

Techniques for electrophoresis and nitrocellulose transfer are disclosed by Maniatis, T., et al. (Molecular Cloning A Laboratory Manual, Cold Spring Harbor, N.Y. (1982)).

EXAMPLE II

Preparation of GPA Proteins

Whole *D. immitis* worms were cultured as described in Example I. Adult worm crude extract was prepared as described above, and subjected to 12% SDS-polyacrylamide gel electrophoresis. The electrophoretic pattern was transferred to nitrocellulose paper and antigens recognizable by antibodies of canine heartworm infected dog sera were visualized by use of an anti-canine-IgG and a coupled peroxidase reaction. Glycoprotein antigens (GPA) are detected as a broad smear of material, the smallest antigen size being about 10 kd. Bands of more intense staining were visualized at 58, 66, 90 and 120 kd.

EXAMPLE III

Preparation of a Hybridoma Capable of Producing Antibodies Specific for the ESP Antiqen ESP antigens were prepared as described in Example I. Approximately 200 ug of ESP sample was purified by SDS-12% polyacrylamide gel electrophoresis. ESP proteins were visualized by soaking the gel in cold 100 mM KCl. The appropriate bands were cut from the gel, thus giving a purification by molecular weight. Portions of the gel were macerated with a polytron tissue grinder in the presence of phosphate-buffered saline. Each of two mice received three immunizations of 10 ug of the 14 kd ESP antigen (0.5 ml/immunization).

The mice were sacrificed and spleen cell/myeloma fusions were carried out as described by Kohler, G. et al. (*Nature,* 256:495 (1975)). Hybridoma supernatents were screened for heartworm specific antibody using ESP-coated polyvinyl plates in a urease-based ELISA. Hybridomas were cloned which secreted anti-14 kd antibody.

In the same manner as described above, GPA proteins were purified and used to immunize mice in order to produce hybridoma lines which secreted monoclonal antibodies directed against the GPA proteins. Two such monoclonal antibody producing cell lines were obtained. On immunoblots following SDS-polyacrylamide gel electrophoresis of crude extracts, GPA was detected by these antibodies as a broad smear of material ranging in molecular weight from 10 kd to 120 kd.

EXAMPLE IV

Characterization of ESP Antigens and GPA Proteins

Sera from heartworm infected dogs was sampled at various times post-infection for the presence of antibodies which recognized the ESP antigens and GPA proteins. Adult worm crude extract of ESP (10–50ug) was run on a 12% SDS-polyacrylamide gel. The proteins were transferred to nitrocellulose and incubated with canine sera. Anti-*D. immitis* antibodies were visualized by monoclonal anti-canine IgG followed by goat anti-mouse IgG-peroxidase. Individual heartworm antigens were thus detected by antibodies in infected dog sera. Both the 14 kd antigen and the GPA proteins were consistently detected and recognized as early as three months post-infection. Since no adult worms are present until approximately five months post-infection, this result indicated that both the 14 kd antigen and the GPA proteins are necessarily expressed in the larval stages of the heartworm organism's development The 14 kd antigen and the GPA protein were further observed to be expressed in all stages of *D. immitis* development.

When *D. immitis* worms are incubated in vivo with $Na^{125}I$ only exterior surface proteins become radiolabeled. Live adult *D. immitis* worms were incubated for 10 minutes at 0° C. with $lmCiNa^{125}I$ and 100 ug/ml chloramine T. The labelling was stopped with $Na_2S_2O_5$ and the $^{125}I$-labelled worms homogenized. An anti-14 kd monoclonal antibody was able to immunoprecipitate radiolabeled 14 kd antigen thus confirming that the 14 kd antigen was a *D. immitis* surface or membrane protein. A corresponding experiment failed to identify any radiolabeled GPA.

Biochemical characterization of the 14 kd antigen has indicated that the protein is a native monomer. Carbohydrate associated with gel filtration fractions was assayed and compared to arabinose and mannose standards. The carbohydrate levels were compared with antigenic activity in the same fractions as measured by anti-GPA and anti-14kD antibodies. A carbohydrate peak of 500 ug/ml GPA was associated with 600 ug/ml GPA protein. Fractions containing 14 kD antigenic activity had little or no measurable carbohydrate (the highest estimate is 25 ug/ml carbohydrate compared to 500 ug/ml protein).

EXAMPLE V

Diagnostic Test for Canine Heartworm Disease

Any of the antigens disclosed in this invention may be used in a diagnostic test for canine heartworm disease. An EIA (enzyme immunoassay) for GPA proteins has been developed. In this assay polyvinyl plates or glass capillary tubes were used as a solid support to which monoclonal antibodies ("MAbs") specific for GPA were affixed. [MAbs were passively adsorbed to polyvinyl or polystyrene plates in 0.1M carbonate buffer pH 9.6; MAbs were covalently coupled to glass capillary tubes that had been previously activated by incubating them with aminopropyltriethoxysilane. MAbs are cross-linked to the activated tubes by glutaraldehyde]. Dog sera were then incubated in the presence of the solid support followed by a subsequent incubation in the presence of a second monoclonal antibody which had been conjugated to the enzyme, urease. Any GPA present in the dog sera binds to the first monoclonal antibody. Using this assay GPA could be detected as early as five months post-infection (the young adult stage of the parasite). Very slight, if any, cross reaction was observed to antigens in sera of dogs infected by parasites such as *Dirofilaria repens, Dipetalonema reconditum* or *Toxocara canis*.

EXAMPLE VI

Purification of the 14 kd Atigen

Monoclonal antibody directed against the 14 kd antigen were prepared as described in Example 3. The monoclonal antibody was affixed to a CNBr-activated sepharose column to form a monoclonal antibody-affinity column. This monoclonal antibody affinity column was capable of purifying the 14 kd antigen to at least 98% homogeneity in a single step from crude worm extracts or cell culture supernatants. Subsequent fractionation, using an HPLC reverse phase column resulted in essentially homogenous preparation. HPLC used a Vydac TM $C^4$ reverse phase column, 10u particle size, 300 A pore size. A gradient elution was performed. Sample was loaded in 0.1% TFA in $H_2O$ and eluted using a linear gradient of acetonitrile with 0.05% TFA.

EXAMPLE VII

A Vaccine for Canine Heartworm Disease

Third stage larvae (L3) of *D. immitis* were dissected from experimentally infected mosquitoes and immediately placed in Iscove's modified Dulbecco's media containing 10% horse serum (GIBCO Laboratories). 100 larvae were transferred to each of 36 wells (using 24-well tissue culture plates) containing 0.5 ml media. Mouse peritoneal macrophages were added to 14 wells ($10^5$ macrophages per well). Affinity-purified monoclonal antibodies, prepared as described above, were added to the wells singly or in mixtures at concentrations of 100 ug/ml or 200 ug/ml. Anti-*D. immitis* 14 kd antigen monoclonal antibodies are designated IDi5, IDi10, IDi37 and 2DI22. Anti-*D. immitis* GPA protein monoclonal antibodies are designated IDi76, 5Di52, 5Di115 and 5Di31. Monoclonal antibodies 2G131 and 6G67 are anti-human chorionic gonadotropin antibodies. The larvae were observed for viability and molting each day following addition of the monoclonal antibodies.

On day 1 of in vitro culture at 37° C., ambient atmosphere, morphology changes in the larvae cuticle were observed in several wells containing the anti-14 kd antigen monoclonal antibodies. These alterations in morphology preceeded the death of the larvae which was evident by day 3 of culture. The result of this experiment are shown in Table 1. The mouse macrophages had no discernable effect, and hence, their presence or absence was unimportant.

TABLE I

| Treatment | # wells | % wells-dead larvae day 3 |
|---|---|---|
| None | 9 | 0 |
| IDi10 (100 ug/ml) | 3 | 100 |
| IDi10 (200 ug/ml) | 3 | 100 |
| IDi10 + IDi5 + IDi37 + 2Di22 (25 ug/ml each) | 3 | 100 |
| IDi10 + IDi76 (100 ug/ml each) | 2 | 100 |
| IDi76 (100 ug/ml) | 2 | 0 |
| IDi76 (200 ug/ml) | 2 | 0 |

TABLE I-continued

| Treatment | # wells | % wells-dead larvae day 3 |
|---|---|---|
| IDi76 + 5Di52 + 5Di115 + 6Di31 (25 ug/ml each) | 2 | 100 |
| 2G131 (100 ug/ml) | 2 | 0 |
| 2G131 (200 ug/ml) | 2 | 0 |
| 6G67 (100 ug/ml) | 3 | 0 |
| 6G67 (200 ug/ml) | 3 | 67 |

Table 2 shows the results of the above experiment grouped by the classes of antibodies used. These results show that both anti-14 kd and anti-GPA antibodies were successful in killing *D. immitis* larvae. Since these antibodies are raised in response to vaccinations by purified 14 kd and GPA proteins (respectively), these results demonstrate the potential efficacy of the 14 kd ESF antigen and GPA proteins in a canine heartworm vaccine.

TABLE II

| Treatment | # wells | % wells-dead larvae day 3 |
|---|---|---|
| None | 9 | 0 |
| anti-14KD | 9 | 100 |
| anti-GPA | 6 | 33 |
| anti-14KD + anti-GPA | 2 | 100 |
| anti-hCG | 10 | 20 |

While the invention has been described in connection with specific embodiments thereof, it will be understood that it is capable of further modifications and this application is intended to cover any variations, uses, or adaptations of the invention following, in general, the principles of the invention and including such departures from the present disclosure has come within known or customary practice within the art to which the invention pertains and as may be applied to the essential features hereinbefore set forth and as follows in the scope of the appended claims.

What is claimed is:

1. An antibody producing cell of the cell line IDi10.

2. The antibody produced by the cell of claim 1 wherein said antibody is capable of binding to a polypeptide associated with infection by *D. immitis*, wherein said polypeptide has a molecular weight selected from the group consisting of approximately 14 kd; approximately 58 kd; approximately 66 kd; and approximately 90 kd; and wherein said polypeptide is detectable in the serum of a canine infected with *D. immitis* three months post-infection.

3. An antibody producing cell of the cell line IDi76.

4. The antibody produced by the cell of claim 3 wherein said antibody is capable of binding to a polypeptide associated with infection by *D. immitis*, wherein said polypeptide has molecular weight selected from the group consisting of approximately 14 kd; approximately 58 kd; approximately 66 kd; and approximately 90 kd; and wherein said polypeptide is detectable in the serum of a canine infected with *D. immitis* three months post-infection.

5. An immunoassay method for diagnosing *D. immitis* infection which comprises:

(A) providing the antibody of any of claim 2 or 4 to a sample suspected of containing a polypeptide associated with infection by *D. immitis*, wherein said polypeptide has a molecular weight selected from the group consisting of approximately 14 kd; approximately 58 kd; approximately 66 kd; and approximately 90 kd; wherein said antibody is capable of binding to said polypeptide; and (B) diagnosing the presence of said infection by determining whether any of said provided antibody binds to said polypeptide.

* * * * *